(12) United States Patent
Donadille et al.

(10) Patent No.: US 8,113,042 B2
(45) Date of Patent: Feb. 14, 2012

(54) GRAVITY MEASURMENT METHODS FOR MONITORING RESERVOIRS

(75) Inventors: Jean-Marc Donadille, Al-Khobar (SA); Saleh B. AlRuwaili, Dammam (SA)

(73) Assignees: Schlumberger Technology Corporation, Sugar Land, TX (US); Saudi Arabian Oil Company, Dhahran (SA)

( * ) Notice: Subject to any disclaimer, the term of this patent is extended or adjusted under 35 U.S.C. 154(b) by 684 days.

(21) Appl. No.: 12/209,261

(22) Filed: Sep. 12, 2008

(65) Prior Publication Data

US 2009/0223291 A1   Sep. 10, 2009

Related U.S. Application Data

(63) Continuation-in-part of application No. 11/864,186, filed on Sep. 28, 2007, now abandoned.

(51) Int. Cl.
 *E21B 49/00* (2006.01)
(52) U.S. Cl. ..................................... 73/152.05
(58) Field of Classification Search ............... 73/152.39, 73/152.41, 152.42, 382 G, 152.05; 166/252.4; 702/6, 10
See application file for complete search history.

(56) References Cited

U.S. PATENT DOCUMENTS

| | | | |
|---|---|---|---|
| 4,397,181 A * | 8/1983 | Caldwell | 73/152.09 |
| 5,351,122 A | 9/1994 | Niebauer et al. | |
| 5,673,191 A * | 9/1997 | Chapin et al. | 702/2 |
| 5,892,151 A | 4/1999 | Niebauer et al. | |
| 5,903,349 A | 5/1999 | Vohra et al. | |
| 6,125,698 A * | 10/2000 | Schweitzer et al. | 73/382 G |
| 6,152,226 A * | 11/2000 | Talwani et al. | 166/252.4 |
| 6,467,543 B1 * | 10/2002 | Talwani et al. | 166/252.4 |
| 6,671,057 B2 | 12/2003 | Orban | |
| 7,047,170 B2 * | 5/2006 | Feldman et al. | 703/10 |
| 7,069,780 B2 | 7/2006 | Ander | |
| 7,155,101 B2 | 12/2006 | Shah et al. | |

OTHER PUBLICATIONS

Hare, J. L., et al., The 4-D microgravity method for waterflood surveillance: A model study for the Prudhoe Bay reservoir, Alaska, Geophysics, Jan.-Feb. 1999, pp. 78-87, vol. 64, No. 1.
Deep Density Borehole Gravity Meter (BHGM), BHGM Survey Brochure, Micro-g LaCoste, Inc., from http://www.microgsolutions.com/bhg-intro2.htm, Sep. 27, 2007 (Date Accessed), pp. 1-14.

* cited by examiner

*Primary Examiner* — John Fitzgerald (57) ABSTRACT

A method of performing gravity surveys in a wellbore is described including performing a time-lapse measurement in a monitoring well in the vicinity of injector wellbores, determining a depth for which the difference of the time lapse measurements changes sign or crosses zero as depth of the anomaly; and using said measurements at other depth points to further determine one or more parameters relating to the location and/or size of a density anomaly caused by injecting fluids through said injector wellbores, thus enabling the sweep of an injected fluid including the occurrence of fingering in the formation.

20 Claims, 5 Drawing Sheets

GRAVITY MEASURMENT METHODS FOR MONITORING RESERVOIRS

CROSS-REFERENCE TO RELATED APPLICATIONS

This is a continuation-in-part of Ser. No. 11/864,186 filed on Sep. 28, 2007, which is hereby incorporated by reference herein in its entirety.

FIELD OF THE INVENTION

The invention relates to the field of gravity measurements to detect changes in a subterranean reservoir.

BACKGROUND

Measurements of the earth's gravitational acceleration, and measurements of differences in the earth's gravitational acceleration (gravity difference) between different depths in the earth or horizontal positions, can be useful in determining the bulk density (or specific gravity) of various earth formations, among other applications. More particularly, measurements of gravity difference between two positions or depths may be used to determine whether oil, water or gas primarily fills pore spaces in the earth formations at various depths and geographic locations in the earth.

Such measurements can also be useful in operations where a fluid, such as a gas, liquid, gel, or foam, is injected into a subterranean formation to enhance or promote the recovery of hydrocarbons with low mobility. To monitor the effectiveness of such treatments it is often desirable to detect at least the depth and/or the position of the fluid front as formed by the injected fluid.

As a practical matter, measuring physical properties of earth formations beneath the surface of the earth is typically performed by a process called "well logging", wherein instruments having various sensors therein are lowered into a wellbore drilled through the earth. The instruments may be lowered into the wellbore and retrieved therefrom at the end of an armored electrical cable in a process known as "wireline" well logging. Alternative conveyance techniques as known in the art include lowering the instruments into the wellbore coupled to the end of a drill pipe, a production tubing or a coiled tubing. The drill pipe conveyance technique, in particular, is commonly referred to as "logging while drilling" when performed during the actual drilling of a wellbore. The well logging instruments, whether wireline or pipe conveyed, may include various devices to measure the earth's gravitational acceleration.

Several gravity measurement tools are commercially available or have been proposed in the prior art. One manufacturer of such tools is for example Lacoste & Romberg who offer a borehole gravity meter (BHGM) under the trade name "Micro-g system".

Other gravity and gravity difference measuring instruments are for example described in U.S. Pat. Nos. 5,351,122 and 5,892,151 both issued to Niebauer et al. and 5,903,349 to Vohra et al. The known gravity tools according to the '151 patent include at least one, preferably several longitudinally spaced apart gravity sensors enclosed in an instrument housing. The gravity sensors are fiber optic interferometry devices, which measure a velocity of a free falling mass by determining, with respect to time, interference fringe frequency of a light beam split between a first path having a length corresponding to the position of the free falling mass, and a second "reference" (fixed length) path. The fringe frequency is related to the velocity of the free falling mass, which in turn can be correlated to earth's gravity by precise measurement of the mass's position and the time from the start of free fall. Measurement of gravity difference is performed by determining a difference in gravity measurements made between two of the individual gravity sensors positioned at locations vertically spaced apart.

Further instruments for gravity and gravity difference measuring are described in co-owned U.S. Pat. No. 6,671,057 issued to Orban including a gravity sensor with a first mass adapted to free fall when selectively released from an initial position. The mass has optical elements adapted to change the length of an optical path in response to movements of the mass. The sensor output is coupled to a beam splitter. One output of the splitter is coupled substantially optically directly to an interferometer. Another output of the splitter is coupled to the interferometer through an optical delay line. The frequency of an interference pattern is directly related to gravity at the mass. A second such mass having similar optics, optically coupled in series to the first mass and adapted to change the path length in opposed direction when selectively dropped to cause time coincident movement of the two masses, generates an interference pattern having frequency related to gravity difference. Further suitable gravity measuring instrument are known for example as U.S. Pat. No. 7,155, 101 to Shah et al.

Methods of using such instruments are described for example in the above '057 patent and in the U.S. Pat. No. 7,069,780 to Ander, and by J. L. Hare et al. in: "The 4-D microgravity method for waterflood surveillance: A model study for the Prudhoe Bay reservoir, Alaska", in Geophysics, Vol. 64, No. 1 (January-February 1999), p. 78-87. In the latter study, the gravity observations are inverted to determine the subterranean density distribution. The inversion used in this prior art is posed as a linear, underdetermined inverse problem with an infinite number of possible solutions. The densities range is subjected to a set of constraints resulting in a constrained, linear system which can be solved using least-square methods. The authors acknowledge that the model parameters determined using the least-square methods are not unique. In addition, the inverse gravity problem is stated to be fundamentally unstable and it is known that any solution based on an optimization approach involves high computational costs.

Given that gravimetric instruments and logging measurements are known per se, it is seen as an object of the present invention to provide new methods for making use of and evaluating gravity logging measurements to determine the depth and/or other geometrical properties of a gravitational anomaly in a subterranean formation. It is a particular object of the invention to provide such methods for monitoring changes in subterranean reservoirs fast and with limited computational costs.

SUMMARY OF INVENTION

According to a first aspect of the invention a method of performing gravity surveys in a wellbore is provided including obtaining a time-lapse measurement of at least a vertical component of the gravitational force in a monitoring well, and determining a depth at which the difference of the time lapse measurement changes sign. It was found that in the presence of a gravity anomaly migrating or moving in a subterranean formation, this depth can be taken as a nominal depth of the anomaly.

It was further found that the position at which the difference of the vertical component of two time-lapse gravity vanishes or changes signs is for the purpose of the present invention equivalent to the depth where the vertical gradient of the difference assumes an extreme value. This extreme value could be either a minimum or a maximum depending on nature of the gravity anomaly, i.e. whether has a positive or negative sign or value. With the representation of the values as per the present invention further standard analytical tools can be applied to determine this depth from the difference measurements.

For the purpose of the present invention the value of the density anomaly is assumed to be prior knowledge. For example, in the field of enhanced oil recovery (EOR), the density of the injected fluids is known together with density, porosity and original fluid content of the original subterranean formation. Taking these values the density or gravity anomaly can be expressed as difference between the formation density and the formation density with the new fluid content. However, the present method is not dependent on the exact method according which the value of the density or gravity anomaly is calculated.

According to another aspect of the invention further parameters relating to the location and/or size of the density anomaly are derived using the time-lapse measurements at three or more further depth points.

The method is based on solving a highly non-linear equation which expresses the difference in the vertical gravity component between two time-lapse measurements as function of three unknowns. In a preferred embodiment these unknowns are the distance of a front of the anomaly from the monitoring well at two different times of measurement and a height of the density anomaly. Because of the assumptions made the method is expected to perform best when a monitored density anomaly can be treated as long, slender block or parallelepiped migrating slowly through the rock formation. For instance, water injected by a long array of injector wells is likely to move in such a manner through a permeable horizontal layer.

Given a sufficient number of independent measuring points, which number is larger than the number of unknowns, well-established methods can be used to solve this equation in three unknowns. The method can thus be used to provide at low computational costs estimates of, for example, the location at different times $t_1$ and $t_2$ and the vertical thickness of an arriving fluid front. Used in isolation, the method provides a fast response and requires only time-lapse gravity readings at three depths in the borehole. In cases of a more complex geometry, the method can still make a valuable contribution by providing either a priori information, a first estimate, or constraints to other inversion methods which invert gravity surveys into density anomalies, for example in conventional time-lapse or 4-D reservoir surveys.

According to a further aspect of the invention a method is provided to model and detect the effects of an inhomogeneous sweep or water-fingering between injector wells and producer wells. In a preferred variant a slender block or parallelepiped is modeled as having a finite width. In a further embodiment of this variant, the presence of several of such blocks or parallelepipeds is modeled. Both aspects of the invention can be combined to increase the efficiency of the detection and modeling of fingering.

DETAILED DESCRIPTION

The following example of a method in accordance with the present invention establishes an analytic relation between the difference of vertical component $\Delta g_z$ of the acceleration due to gravity at an (arbitrary) depth $z_o$ at two different times in a borehole due to a semi-infinite horizontal slab with constant density anomaly $\Delta \rho$.

$$\Delta g_z^{slab}(z_0; x_{min}, x_{max}, h) = G \cdot \Delta \rho \begin{bmatrix} x_{max} \cdot \ln\left(\frac{x_{max}^2 + (h-z_0)^2}{x_{max}^2 + (h+z_0)^2}\right) + \\ x_{min} \cdot \ln\left(\frac{x_{min}^2 + (h+z_0)^2}{x_{min}^2 + (h-z_0)^2}\right) + \\ 2(h-z_0) \cdot \left\{ \begin{array}{l} \tan^{-1}\left(\frac{x_{max}}{h-z_0}\right) - \\ \tan^{-1}\left(\frac{x_{min}}{h-z_0}\right) \end{array} \right\} + \\ 2(h+z_0) \cdot \left\{ \begin{array}{l} \tan^{-1}\left(\frac{x_{min}}{h+z_0}\right) - \\ \tan^{-1}\left(\frac{x_{max}}{h+z_0}\right) \end{array} \right\} \end{bmatrix} \quad [1]$$

The variables $x_{min}$ and $x_{max}$ denote the algebraic distance (meaning they can take positive or negative values) from the fluid front to a monitoring well where borehole gravity readings have been taken in time-lapse. They correspond to times $t_2$ and $t_1$ respectively. In the example, positive values of $x_{min}$ (respectively, $x_{max}$) refer to cases where the fluid front have not reached the monitoring well at time $t_2$ or $t_1$, respectively, while negative values refer to the opposite situation.

In the present example, a borehole gravimetry survey includes the measurement of the vertical component $g_z$ of the acceleration due to gravity. Subtracting values obtained at different times at a depth z gives a differential gravity vector $\Delta g_z = g_z(t_2) - g_z(t_1)$. Having determined $\Delta g_z$ through measurement, the equation (1) can be evaluated to gain $x_{min}$, $x_{max}$ and h, which denotes the half-thickness of the density anomaly, directly from the borehole gravity measurements.

The above relation can be also expressed as equation for the spatial gradient of the differential gravity vector, e.g. $(\Delta g_z(z=z_o+1) - \Delta g_z(z=z_o-1))/2l$.

At any fixed value $z_o$, the functional $\Delta_{gz}$ as defined above is continuous in the variables $x_{min}$, $x_{max}$ and h. Moreover (except for $z_o = z_c$), it is strictly monotonic in one variable while the other two are held constant. This ensures that the set $\Delta g_z^{slab}(z_0; x_{min}, x_{max}, h) - \Delta g_z^{meas}(z_0) = 0$ is a (curved) continuous surface in the $(x_{min}, x_{max}, h)$ space. Taking the intersection of three sets corresponding to three different values of $z_o$ yields the solution $(x_{min}^*, x_{max}^*, h^*)$.

Figure 1:
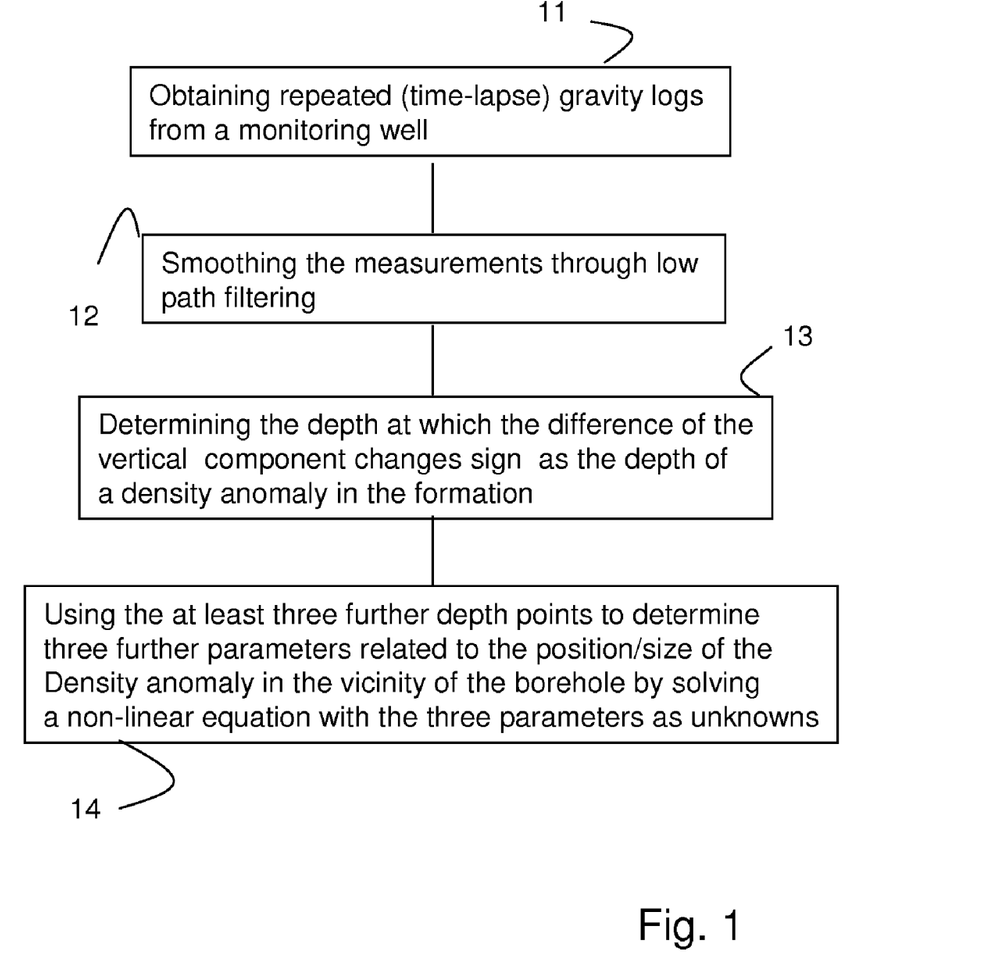
FIG. 1 is a flow diagram illustrating steps in accordance with an example of the present invention.

In order to evaluate the above relations, the following steps as illustrated in FIG. 1 can be performed:

1- From the measurements of borehole gravity (i.e. the vertical component of the gravity field) at the two different times, create the time-lapse differential gravity measurement: $\Delta g_z^{meas} = g_z^{meas}(t_2) - g_z^{meas}(t_1)$ for multiple depth points $z_o$.

2- Optionally apply any kind of smoothing processing or low-pass filter on the curve $\Delta g_z^{meas}(z_o)$
3- The central vertical position of the density anomaly is given by the unique depth $z_c$ where $\Delta g_z^{meas}(z_c)=0$ or changes sign (or equivalently where the vertical gradient $\nabla z(\Delta g_z^{meas}(z_c))$ is an extremum)
4- Obtain the half-thickness h of the slab, the algebraic distance $x_{min}$ (respectively, $x_{max}$) of the fluid front from the borehole at time $t_2$ (respectively, $t_1$) where gravity measurements have been recorded by solving for $(x_{min}^*, x_{max}^*, h^*)$ the set of nonlinear equations.

The above steps 1-4 are shown as steps 11-14 in the flow chart in FIG. 1.

Figure 2A:
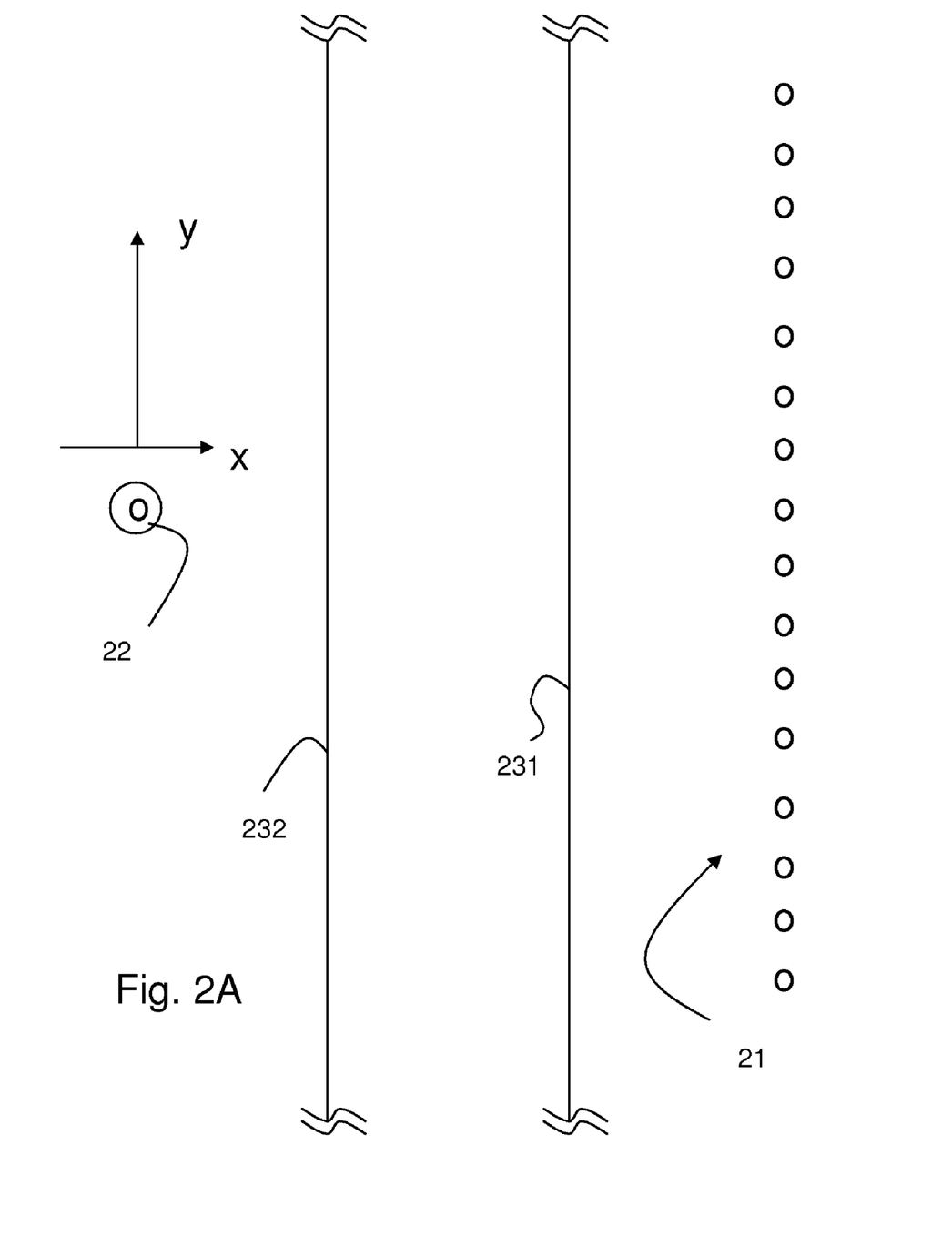
FIGS. 2A and 2B are schematic views illustrating the evolution of a fluid front in a subterranean reservoir as measured by the present invention.

FIGS. 2A and 2B illustrate a borehole gravity survey using the steps as described above. The schematic horizontal cross-section through a subterranean layer of FIG. 2A shows an array of injector wells 21 used to inject a fluid with a density anomaly having a difference in the bulk density before and after flooding $\Delta\rho$. A part of the fluid front caused by this injection is shown as line 231 at a distance $x_{max}$ at the time $t_1$. The time $t_1$ is the time of the first gravity logging measurement in the monitoring well 22. The distance $x_{max}$ is taken relative to a coordinate system which fixed to the monitoring well 22. The front of the injected fluids moves further and further away from the injector wells 21 as new fluid is either pumped into the formation or other fluids (not shown) are pumped out of a production well (not shown). A part of the fluid front caused by this injection at a later time $t_2$ is shown as line 232 at a distance $x_{min}$. The time $t_2$ is the time of the second or time-lapse gravity logging measurement in the monitoring well 22.

Figure 2B:
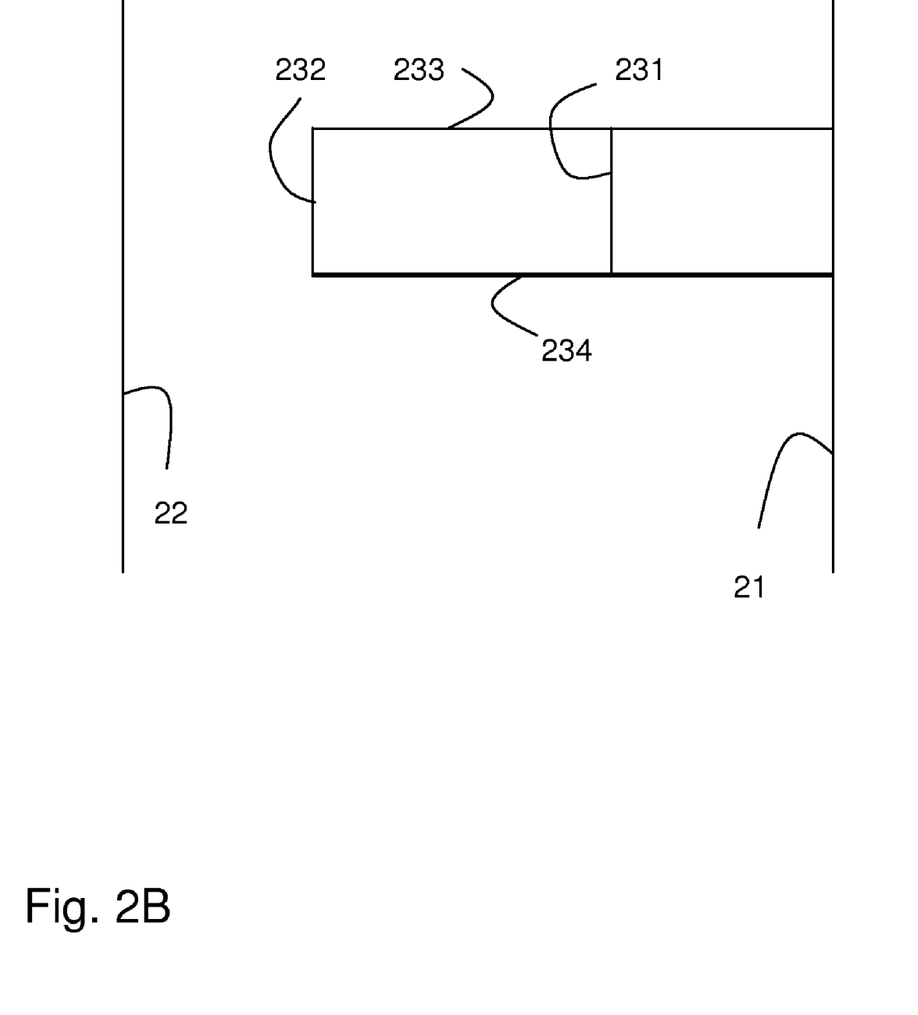

FIG. 2B illustrates a schematic vertical cross-section through the subterranean layer. In this view only one well of the array 21 of injector wells is visible. The fluid front at times $t_1$ and $t_2$ are shown as lines 231 and 232, respectively. In this view the height h of the density anomaly is visible as half the vertical distance between lines 233 and 234. It should be emphasized that the fluid or density distribution as shown is a geometrical approximation to facilitate the mathematical treatment of the problem as per equation [1]. A real injection operation can at best be approximated by the geometry of the fluid distribution as shown in FIGS. 2A and 2B.

For the calculation, a further assumption is made in that the zone is treated as if extending to infinity in the y-direction, which is taken to be the horizontal direction perpendicular to the direction between injector well 21 and monitoring well 22. While the validity of the assumption depends on the circumstances of the injection operations it is likely to be valid when the array of injectors 21 is spread in this direction. It should be further noted that the gravity response function decreases in proportion to $1/r^2$. Thus the contribution from a volume of formation located far away from the monitoring well decreases rapidly with the distance from the monitoring well.

The time lapse measurements for the purpose of this invention are conducted typically at least 7 days apart, usually however more than 1 month apart. In any case, the repeat measurement is only viable if and when the fluid front has moved or is expected to have moved a significant distance so as to be resolved using the available technology. The measurements as can be performed using commercially available logging tools as described in the background above.

Figure 3:
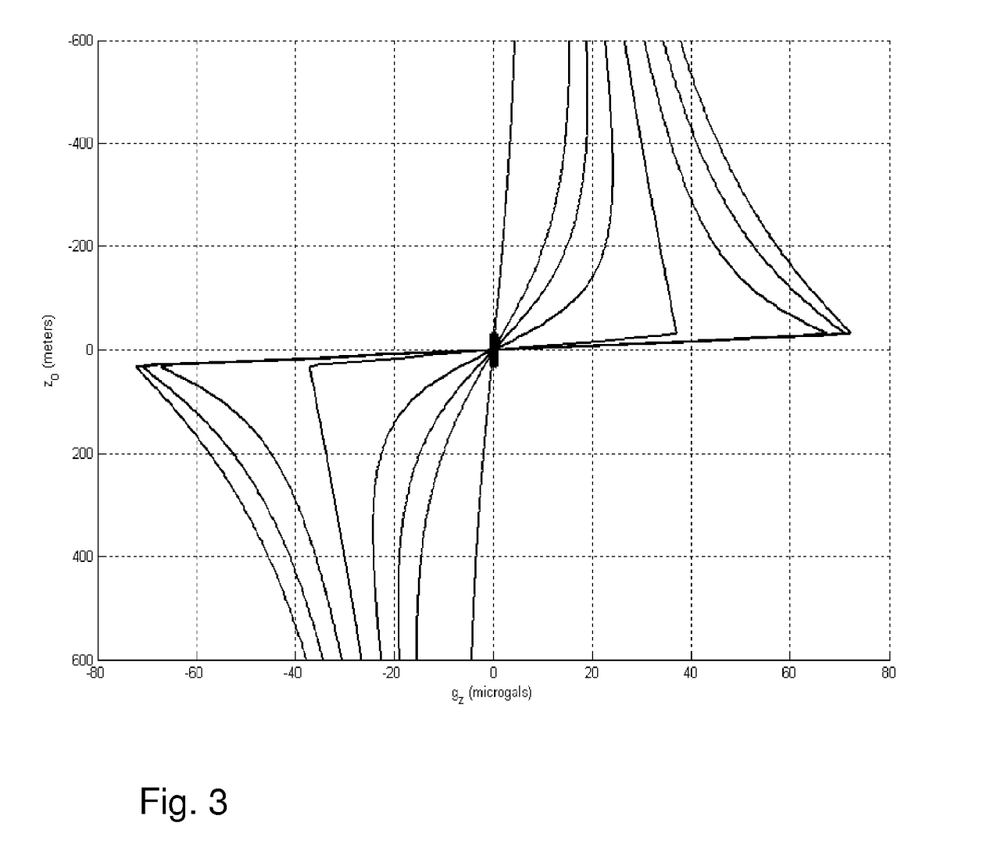
FIG. 3 is a plot of a numerical example in accordance with the present invention.

In FIG. 3 there is shown a plot of values of $\Delta g_z$ in a borehole as computed from equation [1]. In this synthetic example the density anomaly is assumed to be caused by a horizontally extending parallelepiped as depicted in FIG. 2 above. The anomaly is defined in this example as the difference between the bulk density of the flooded formation and the bulk density of the formation prior to flooding and its numerical value is $\Delta\rho=0.03$ g/cc. The height of the fluid front in this example is 30 m and its initial position is at $x_{max}=1200$ m.

The responses shown correspond to eight values of $x_{min}$ (800 m, 300 m, 200 m, 100 m, 0 m, −100 m, −200 m, −300 m) with the depth $z_o$ of the measurement relative to the assigned depth of the anomaly used as ordinate and $\Delta g_z$ as abscissa. The vertical positioning of the anomaly is indicated by a central bar. The response for 800 m is the most central line and the response for −300 m at the outer fringe of the graph with the other responses ordered accordingly.

The results show that the values are symmetrical around the zero vertical position which is defined above as being level with the nominal depth of the anomaly. When evaluating with limited number of gravity measurements, it is therefore preferable to use gravity measurements at depths which are not symmetrically positioned with the respect to the relative $z_o=0$ depth. One of the measurements is equally best taken to be at the wide end of the spread of the gravity log to ensure that it is the largest possible distance from the depth where the relative $z_o=0$.

Figure 4:
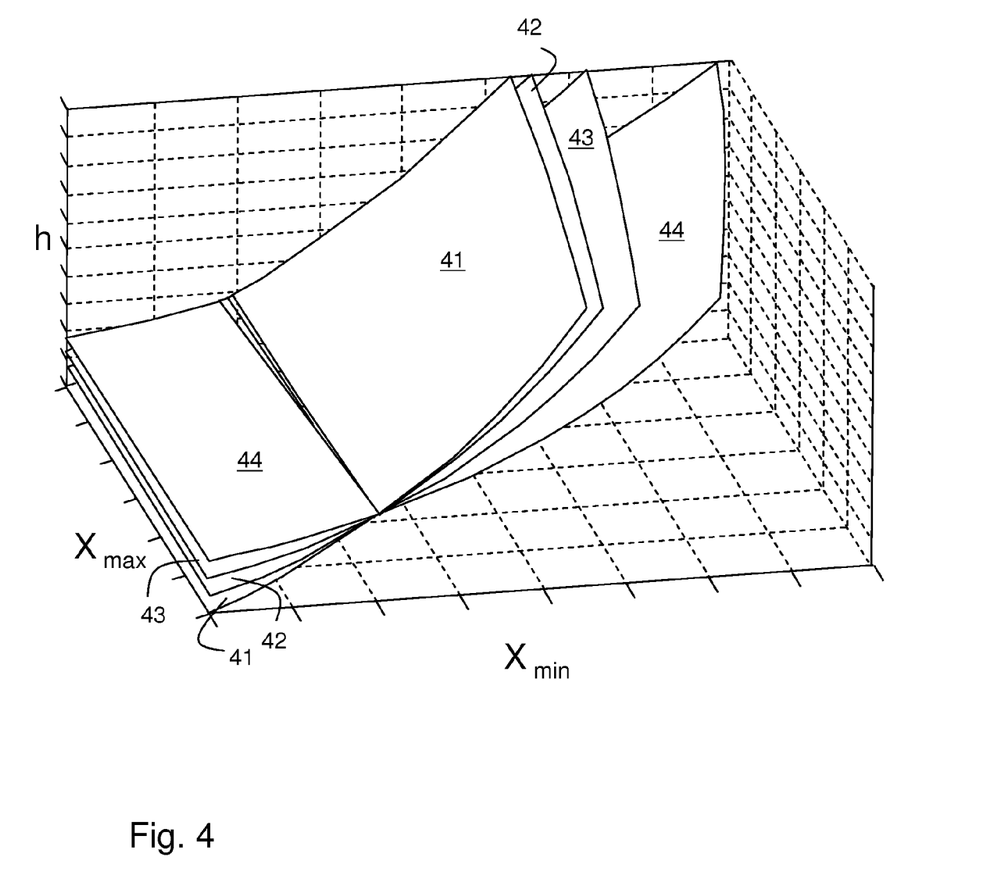
FIG. 4 illustrates how geometrical parameters characterizing a fluid front are determined in accordance with an example of the present invention.

As shown in FIG. 4, for every given value of $z_0$ (depth) equation [1] defines a smooth surface in the three-dimensional space of h, $x_{min}$ and $x_{max}$. Fours sets of points 41-44 obtained at $z_o=5$ m, 50 m, 100 m and 200 m, respectively, for a 60 m-thick density anomaly ($\Delta\rho=0.03$ g/cc) are shown in the figure. The values of $x_{min}$, $x_{max}$ and h can be recovered from the measured data by solving the non-linear equation [1] if the measured $\Delta_{gz}$ is taken from at least three different depths. The point where all surfaces intersect yields the solution, which in this example is h=30 m, $x_{min}=100$ m and $x_{max}=600$ m. The accuracy of these values depends on how well the intersection of the above surfaces 41-44 is defined. As expected, for this particular example the method resolves $x_{min}$ better than $x_{max}$ as the gravity measurement is much less sensitive to features located at 600 m distance from the borehole than to features located at 100 m. A higher number of depth points is likely to increase the accuracy of the solution in a real measurement.

Alternatively to equation [1] above the effect of gravity anomalies can be also modeled using a different model based on a finite slab width 2 w (+w ; −w) in a direction orthogonal to x and z, i.e., in y direction.

$$\Delta g_z^{Finite\ slab}(z_0; x_{min}, x_{max}, h) = \quad\quad [2]$$

$$2G \cdot \Delta\rho \sum_{x=x_{min}+\Delta x_i}^{x=x_{max}} \left\{ \ln\left(\frac{\sqrt{x^2+(h-z_0)^2+w^2}-w}{\sqrt{x^2+(h-z_0)^2+w^2}+w}\right) - \ln\left(\frac{\sqrt{x^2+(h+z_0)^2+w^2}-w}{\sqrt{x^2+(h+z_0)^2+w^2}+w}\right) \right\} \Delta x$$

where $\Delta x=(x_{max}-x_{min})/N$. N is a large integer number, chosen to make $\Delta x$ a small discretization step along x for minimizing the error introduced by approximating an integral through summation. One way to obtain N is by obtaining a first order approximation of $(x_{max}-x_{min})$ by solving equation [1] above assuming an infinite water-body along the y-direction; then choosing a value for N that would constrain $\Delta x$ to a desired discretization step ($\Delta x=(x_{max}-x_{min})/N$) being less than or equal to a pre-determined tolerance or accuracy value.

Therefore, a combination of solutions to [1] and [2] can be utilized for identifying the shape of water-body approaching (or moving away from a vertical well equipped with gravity measurement sensor(s) providing more than one data point across the gravity anomaly.

This variant of the invention can be extended to include and hence detect several blocks or parallelepipeds. The invention is particularly suitable for modeling for example water fingering as a result of an inhomogeneous water sweep between injector and producer wells.

The above example can be varied in a number of ways, including but not limited to using it to establish the tail position of a fluid layer and to derive further control parameters such as pumping time and pressure for an enhanced oil recovery or fluid injection operation.

What is claimed is:

1. A method of monitoring a subterranean density anomaly, comprising:
   a) combining vertical components of a first gravity logging measurement in a monitoring wellbore at a first time and a second gravity logging measurement in said monitoring wellbore at a second time to form a set of depth-related values equivalent to the difference of said vertical components;
   b) determining a depth corresponding to the depth at which a difference of said vertical components changes sign; and
   c) assigning said depth as the depth of said density anomaly.

2. A method of monitoring a subterranean density anomaly in accordance with claim 1, comprising the step of using the assigned depth as initial condition and/or constraint in a further process of deriving parameters relating to location and/or size of said density anomaly through an inversion using essentially the complete gravity logging measurements.

3. A method of monitoring a subterranean density anomaly in accordance with claim 1, wherein said density anomaly is a fluid injected into a subterranean formation using one or more injector wellbores.

4. A method of monitoring a subterranean density anomaly in accordance with claim 1, further comprising the step of reducing noise or fluctuations in the gravity measurements.

5. A method of monitoring a subterranean density anomaly in accordance with claim 1, further comprising the step of reducing noise or fluctuations in the gravity measurements by low pass filtering the measurements prior to determining the depth of the anomaly.

6. A method of monitoring a subterranean density anomaly in accordance with claim 1, wherein further parameters relating to the size of said density anomaly are derived by processing values from at least three further depths from the set.

7. A method of monitoring a subterranean density anomaly in accordance with claim 6, wherein the further parameters are selected from a group consisting of the distance of said density anomaly from the monitoring wellbore at the first and the second time, the height of said density anomaly and any geometrical equivalents of this properties.

8. A method of monitoring a subterranean density anomaly in accordance with claim 6, wherein the further parameters are determined assuming that said density anomaly extends into infinity in one horizontal direction.

9. A method of monitoring a subterranean density anomaly in accordance with claim 6, wherein the further parameters are determined assuming that said density anomaly has an equal height at the first and the second time.

10. A method of monitoring a subterranean density anomaly in accordance with claim 6, wherein at least one of the at least three different further values is selected from within a distal third of depths values of the gravity logging measurement relative to the assigned depth.

11. A method of monitoring a subterranean density anomaly in accordance with claim 6, wherein the at least three further depths are selected to be asymmetric relative to the assigned depth.

12. A method of monitoring a subterranean density anomaly in accordance with claim 6, comprising the step of using the further parameters as initial condition and/or constraints in a further process of deriving parameters relating to location and/or size of said density anomaly through an inversion using essentially the complete gravity logging measurements.

13. A method of monitoring a subterranean density anomaly in accordance with claim 6, further comprising the step of controlling a fluid injection process using control parameters at least partially derived from the further parameters.

14. A method of monitoring a subterranean density anomaly in accordance with claim 6, wherein the further parameters are determined by representing the difference of the vertical components of the gravity logging measurements at the first time and the second time as a non-linear function in at least one of depth and three further parameters representative of the size of the density anomaly.

15. A method of monitoring a subterranean density anomaly in accordance with claim 14, wherein the three parameters represent the distances of said density anomaly to the monitoring wellbore at the first and the second time and a height of said density anomaly.

16. A method of performing gravity surveys in a wellbore, comprising:
   a) selecting a wellbore in the vicinity of injector wellbores;
   b) performing time lapse gravity surveys in said selected wellbore;
   c) determining a depth of a density anomaly as the depth at which the difference between values of said time lapse surveys change sign; and
   d) using said measurements to determine further parameters relating to the location and/or size of a density anomaly caused by injecting fluids through said injector wellbores.

17. A method of detecting a fluid sweep in a formation between one or more injector wells and one or more producer wells including the step monitoring subterranean density changes, wherein for the purpose of locating and determining dimensions of a density anomaly, said density anomaly is treated as a parallelepiped with finite height and length.

18. A method of detecting a fluid sweep in a formation in accordance with claim 17, wherein said density anomaly is treated as a parallelepiped with finite height, width and length.

19. A method of detecting a fluid sweep in a formation in accordance with claim 17, wherein said density anomaly is treated as a parallelepiped with finite height, width and length and wherein the method is adapted to detect an inhomogeneous sweep of the fluid.

20. A method of detecting a fluid sweep in a formation in accordance with claim 17, wherein said density anomaly is treated as a parallelepiped with finite height, width and length and wherein the method is adapted to detect an fingering of the fluid in the formation.

* * * * *

UNITED STATES PATENT AND TRADEMARK OFFICE
CERTIFICATE OF CORRECTION

| | | |
|---|---|---|
| PATENT NO. | : 8,113,042 B2 | Page 1 of 1 |
| APPLICATION NO. | : 12/209261 | |
| DATED | : February 14, 2012 | |
| INVENTOR(S) | : Jean-Marc Donadille and Saleh B. Al-Ruwaili | |

It is certified that error appears in the above-identified patent and that said Letters Patent is hereby corrected as shown below:

Title page, Item [54] the title, "GRAVITY MEASURMENT METHODS FOR MONITORING RESERVOIRS," should read, "GRAVITY MEASUREMENT METHODS FOR MONITORING RESERVOIRS."

On the Title page, Item [75] the second inventor name, "Saleh B. AlRuwaili," should read, "Saleh B. Al-Ruwaili."

Signed and Sealed this
Fifth Day of March, 2013

Teresa Stanek Rea
*Acting Director of the United States Patent and Trademark Office*

UNITED STATES PATENT AND TRADEMARK OFFICE
CERTIFICATE OF CORRECTION

PATENT NO.        : 8,113,042 B2                                         Page 1 of 1
APPLICATION NO.   : 12/209261
DATED             : February 14, 2012
INVENTOR(S)       : Jean-Marc Donadille and Saleh B. Al-Ruwaili It is certified that error appears in the above-identified patent and that said Letters Patent is hereby corrected as shown below:

ON THE TITLE PAGE

Item [54] and in the specification, Column 1, lines 1 and 2, the title, "GRAVITY MEASURMENT METHODS FOR MONITORING RESERVOIRS," should read, "GRAVITY MEASUREMENT METHODS FOR MONITORING RESERVOIRS."

Item [75] the second inventor name, "Saleh B. AlRuwaili," should read, "Saleh B. Al-Ruwaili."

This certificate supersedes the Certificate of Correction issued March 5, 2013.

Signed and Sealed this
Ninth Day of April, 2013

Teresa Stanek Rea
*Acting Director of the United States Patent and Trademark Office*